US012779249B2

(12) United States Patent
Popescu

(10) Patent No.: US 12,779,249 B2
(45) Date of Patent: Nov. 3, 2026

(54) METHOD AND DEVICE FOR REAL-TIME MONITORING OF AN APPLIED RADIATION DOSE

(71) Applicant: Siemens Healthineers AG, Forchheim (DE)

(72) Inventor: Stefan Popescu, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/973,448

(22) Filed: Dec. 9, 2024

(65) Prior Publication Data

US 2025/0205516 A1 Jun. 26, 2025

(30) Foreign Application Priority Data

Dec. 22, 2023 (EP) .................................... 23219623

(51) Int. Cl.
*A61N 5/10* (2006.01)

(52) U.S. Cl.
CPC .... *A61N 5/1049* (2013.01); *A61N 2005/1055* (2013.01)

(58) Field of Classification Search
CPC .......... A61N 2005/1055; A61N 5/1048; A61N 5/1049; A61N 5/1064; A61N 5/1071; G01R 33/4808; G01R 33/4804
See application file for complete search history.

(56) References Cited

U.S. PATENT DOCUMENTS

| | | | | |
|---|---|---|---|---|
| 2005/0197564 A1* | 9/2005 | Dempsey | ............. | A61B 5/4836 378/65 |
| 2010/0125191 A1* | 5/2010 | Sahin | ..................... | G01R 33/48 600/422 |
| 2014/0012126 A1 | 1/2014 | Popescu | | |
| 2014/0114177 A1* | 4/2014 | Chen | .................... | A61B 5/0051 600/421 |

(Continued)

FOREIGN PATENT DOCUMENTS

| | | |
|---|---|---|
| DE | 102012211581 A1 | 1/2014 |

OTHER PUBLICATIONS

Vieira, S.L. et al. "Evaluation of the Dynamic Mechanical Behavior of Polymer Gel Dosimeter", Pan American Health Care Exchanges, PAHCE 2011—Conference, Workshops, and Exhibits. Cooperation / Linkages: An Independent Forum for Patient Care and Technology Support, pp. 287-290, (2011) (Year: 2011).*

(Continued)

*Primary Examiner* — Keith M Raymond
*Assistant Examiner* — Milton Truong
(74) *Attorney, Agent, or Firm* — Lempia Summerfield Katz LLC

(57) ABSTRACT

Methods and systems are disclosed for monitoring in real time a radiation dose applied by an irradiation device in a target area by a magnetic resonance tomography unit. The irradiation device is configured to emit the radiation in a form that is modulated in intensity in the acoustic frequency range. The irradiation device radiates modulated radiation into the target area, during which the magnetic resonance tomography unit captures a magnetic resonance image of the target area using a sequence that is sensitive to an amplitude of a deflection of tissue in the target area.

17 Claims, 6 Drawing Sheets

(56) References Cited

U.S. PATENT DOCUMENTS

| | | | | |
|---|---|---|---|---|
| 2015/0217136 | A1* | 8/2015 | Stanescu | A61B 6/4417 324/309 |
| 2017/0000376 | A1* | 1/2017 | Partanen | A61B 5/0036 |
| 2017/0165504 | A1 | 6/2017 | Dollinger | |
| 2020/0352442 | A1* | 11/2020 | Grodzki | A61B 5/0036 |
| 2023/0125842 | A1* | 4/2023 | Dempsey | G01R 33/50 600/411 |
| 2023/0277875 | A1 | 9/2023 | Schauer | |

OTHER PUBLICATIONS

Hickling, S. et al. "Ionizing radiation-induced acoustics for radiotherapy and diagnostic radiology applications", Med. Phys. 45 (7), e707-e721, (2018) (Year: 2018).*

Vieira, S.L. et al. "Quantitative magnetic resonance elastography for polymer-gel dosimetry phantoms", Medical Engineering and Physics, 66, 102-106, (2019) (Year: 2019).*

Mayo Clinic "Magnetic resonance elastography", https://www.mayoclinic.org/tests-procedures/magnetic-resonance-elastography/about/pac-20385177, p. 1-10, (2022).

Plewes, D. B., et al. "Quantitative magnetic resonance imaging of ultrasound fields." In 1997 IEEE Ultrasonics Symposium Proceedings. An International Symposium (Cat. No. 97CH36118), vol. 2, pp. 1297-1300. IEEE, 1997.

Wikipedia "Hyperthermia Therapy", https://en.wikipedia.org/wiki/Hyperthermia_therapy, Obtained Jun. 2023. pp. 1-8.

Zhang, Wei, et al. "Real-time, volumetric imaging of radiation dose delivery deep into the liver during cancer treatment." Nature biotechnology 41.8 (2023): 1160-1167.

* cited by examiner

METHOD AND DEVICE FOR REAL-TIME MONITORING OF AN APPLIED RADIATION DOSE

The present patent document claims the benefit of European Patent Application No. 23219623.8, filed Dec. 22, 2023, which is hereby incorporated by reference in its entirety.

TECHNICAL FIELD

The disclosure relates to a method for monitoring in real time, by a magnetic resonance tomography unit, a radiation dose applied by an irradiation device in a target area. Additionally, the disclosure relates to a system composed of a magnetic resonance tomography unit and an irradiation device. The irradiation device is configured to emit the radiation in pulses. The magnetic resonance tomography unit is configured to capture a magnetic resonance image of the target area during the irradiation.

BACKGROUND

The aim in radiation therapy is to irradiate a target, (e.g., a tumor), with a defined minimum dose while minimizing damage to surrounding tissue as far as possible. To this end, in preparation for the irradiation, the precise location of the organs is detected, for example, using computed tomography or magnetic resonance tomography. Model-calculations are used to produce from this data a radiation treatment plan, in which the irradiation directions and intensities for the treatment are ascertained. As a result of movements of individual organs and also errors in the assumptions, for example, about distinct properties of the individual tissue types, the actually applied radiation doses differ from these model-calculations.

The article "Real-time, volumetric imaging of radiation dose delivery deep into the liver during cancer treatment-|Nature Biotechnology" (https://www.nature.com/articles/s41587-022-01593-8) discloses a method for detecting a dose distribution by the acoustic waves produced in the tissue by the radiation, or more precisely by the momentum and energy transferred therefrom.

Document DE 10 2012 211581 A1 describes a method for elastography. The method includes applying a radiofrequency pulse in order to manipulate a transverse magnetization in the defined region and applying at least one further radiofrequency pulse with spatial selectivity in the amplitude in order to produce shear waves in the defined region. The method includes detecting a magnetic resonance signal from the defined region and determining on the basis of the magnetic resonance signal a quantity that describes the tissue elasticity in the defining region.

Magnetic resonance tomography units are imaging devices that, in order to image an object under examination, align nuclear spins of the object under examination with a strong external magnetic field, and use an alternating magnetic field to excite the nuclear spins to precess about this alignment. The precession or return of the spins from this excited state into a lower-energy state in turn produces as a response an alternating magnetic field, which is received by antennas.

Gradient magnetic fields are used to apply spatial encoding to the signals, so that the received signal may subsequently be associated with a volume element. The received signal is then analyzed, and a three-dimensional imaging representation of the object under examination is provided.

SUMMARY AND DESCRIPTION

It is an object of the present disclosure to make radiation therapy more reliable.

The object is achieved by a method and by a system as disclosed herein. The scope of the present disclosure is defined solely by the appended claims and is not affected to any degree by the statements within this summary. The present embodiments may obviate one or more of the drawbacks or limitations in the related art.

The method is intended for monitoring in real time, by a magnetic resonance tomography unit, a radiation dose applied by an irradiation device in a target area. Real-time monitoring is considered here to be monitoring that captures while a single irradiation session is still in progress the dose applied up to that point, and which makes it possible to change this dose, or to change the further irradiation based on the captured dose. The dose may be captured for time segments of less than 10 seconds, less than 1 second, or less than 0.1 seconds. For example, the dose is ascertained for each one of the radiation pulses described below.

The irradiation device is configured to emit ionizing radiation for treating tumors, for example. Ionizing radiation is understood to mean photons with an energy greater than 1 keV, greater than 10 keV, greater than 100 keV, or greater than 1 MeV. Such photons may be produced, for example, by an X-ray tube or a charged-particle accelerator or by a radioactive element. Ionizing particle beams of high-energy beta particles or electrons, or of protons, alpha particles or even heavy ions are also conceivable, however. High-energy is understood to mean here particles with a kinetic energy greater than 1 keV, greater than 10 keV, greater than 100 keV, or greater than 1 MeV.

The irradiation device is configured to emit the emitted radiation in an intensity-modulated form. This shall be understood to mean that the radiation power of the source varies with time, e.g., by at least 10%, by at least 30%, or by at least 50%. The intensity may vary by up to 100%, in other words, the radiation is emitted in pulses. The frequency of the variations lies in the acoustic frequency range, e.g., in a range of 1 Hz to 100 kHz or in a range of 10 Hz to 10 kHz. In particular, the frequency is chosen such that momentum and/or energy transferred by the radiation may cause a mechanical movement or deflection in the tissue in the target area, which may then also be captured by magnetic resonance imaging. Shear or transverse oscillation and also compression or longitudinal waves are conceivable here. The deflection may be considered to be a single deflection of volume elements of the tissue for one beam pulse with subsequent return to the rest position, in the form of an exponentially damped oscillation or in an asymptotic manner. A periodic motion in the form of an oscillation is also conceivable, however.

The frequency of the modulation or the beam pulses may also match in particular a frequency of an image capture sequence of the magnetic resonance tomography unit, or be synchronized with the course of the sequence, which sequence is used in capturing a magnetic resonance image, as described below. For example, the irradiation may be pulsed, and the pulse may be at a predefined time interval from a reference point in the sequence, for example, from an RF pulse and/or a gradient pulse. It is also conceivable, however, that the predefined time interval varies in a predefined manner, for example, in order to modify a phase during the sampling. The synchronization may be controlled by the magnetic resonance tomography unit or the irradiation device via a signal connection between magnetic resonance tomography unit and irradiation device, or in a bilateral synchronization protocol. Specific safety requirements for the irradiation device may be taken into account in this process in order to rule out a risk to the patient through over-long irradiation.

The magnetic resonance tomography unit or the system composed of magnetic resonance tomography unit and irradiation device is additionally configured to capture a magnetic resonance image of the target area during the irradiation. In other words, the magnetic resonance tomography unit and the irradiation device are arranged relative to one another such that the irradiation of a patient may take place while the patient is located in an image capture region of the magnetic resonance tomography unit, for instance in the patient tunnel. In addition, the magnetic resonance tomography unit has access for the radiation to the image capture region.

The method includes applying modulated radiation by the irradiation device into the target area.

Simultaneously, in the method, a magnetic resonance image of the target area is captured by the magnetic resonance tomography unit. "Simultaneously" may be understood to be mean here that at least parts of the image capture sequence take place during the irradiation. The sequence is configured such that the sequence may capture an amplitude of a deflection or oscillation of a tissue in the target area at a frequency of the modulation of the irradiation modulation, i.e., the magnetic resonance signal depends on the amplitude of the deflection. Examples of sequences for capturing the deflection include a gradient echo, echo-planar imaging (GRE-EPI) sequence, a spin echo sequence, or a modified echo-planar imaging (EPI) sequence, as described below with reference to the figures. The term "simultaneously" may be understood to mean that the irradiation or the pulses are interleaved with the image capture sequence in a predefined manner. In certain examples, applying the radiation and image acquisition may be synchronized. This may be done via a signal connection between irradiation device and magnetic resonance tomography unit. One of the devices may be the master, (e.g., the irradiation device for safety reasons), or the synchronization may be carried out between both devices by a synchronization protocol in intercommunication or by a further synchronization unit.

In a further act, a controller, which may be part of the magnetic resonance tomography unit or else separate from the unit, ascertains a dose distribution of the radiation in the target area from the captured magnetic resonance image, or on the basis of the deflection, or its amplitude, captured in the magnetic resonance image. For example, the dose distribution may be shown in the form of a 2-dimensional or 3-dimensional map as a spatial distribution or spatially resolved information about the radiation dose.

The applied radiation dose is related to the amplitude of the captured deflection by a function, since the deflection is brought about by the action of the radiation. A deflection caused by thermal action, i.e., an expansion resulting from heating, is conceivable. The expansion brings about a displacement of tissue from a center of the heating. It is also conceivable that a direct transfer of momentum from the radiation to the tissue is induced, since even high-energy photons have momentum, although this is especially the case for particle beams containing particles with a rest mass. The deflection may also have a mathematically complex dependence on the radiation dose, in particular in the case of thermal action. A radiation dose may be determined therefrom by a calibration or mathematical modeling. Since the deflection depends on the power and/or the momentum of the beam, the dose is obtained by integrating the deflection over time. This integration may be determined mathematically, or already by the sequence used for the capture, as explained in greater detail below with reference to the figures. A spatial distribution or map of the applied radiation dose may thus be determined from the captured amplitude distribution, for instance by the controller of the magnetic resonance tomography unit or another controller.

The method advantageously uses the radiation-induced deflection and its capture by a magnetic resonance sequence to capture in real time and in relation to position a radiation dose applied in a patient.

In an embodiment of the method, the method additionally includes capturing, by the magnetic resonance tomography unit, a reference magnetic resonance image of the target area without radiation being applied simultaneously by the irradiation device. The capture of the reference magnetic resonance image may be performed using a sequence that is identical except for applying the radiation.

The reference magnetic resonance image is then used in ascertaining the dose power. The effect of the radiation-induced deflection and its repercussions are small even with optimized sequences, and may be masked by other effects such as B0 or B1 inhomogeneities. Advantageously, these interference effects may be reduced advantageously by forming the difference between image data with and without applying radiation.

In an embodiment of the method, a sequence containing motion encoding gradients (MEG) is used in capturing the magnetic resonance image and capturing the reference magnetic resonance image. A motion encoding gradient is configured to modify nuclear spins in a slice or a volume element in terms of the phase and/or amplitude of their precession so that a spatial displacement of the volume element or slice may be captured by measuring the magnetic resonance signals. A gradient along the deflection may be used for this purpose, so that nuclear spins that are subject to a deflection are exposed at least temporarily to a different magnetic field, B0 plus the gradient strength multiplied by an amplitude of the deflection, and thus experience a phase change in relation to nuclear spins that are not deflected (in the direction of the gradient). Sequences containing such gradients are known, for example, from the documents on elastography cited in the beginning. The motion encoding gradient may be parallel to the direction of the deflection. It is also conceivable to employ image captures using gradients in three dimensions in order to capture the spatial thermal expansion. An image capture using the applied MEG(s) is performed while the beam is incident in the target area.

Magnetic resonance sequences used for diffusion measurement or spin labeling sequences such as for flow MRI are also conceivable.

In the capturing a magnetic resonance image and/or the capturing a reference magnetic resonance image, the capture is performed with inverted polarity of a motion encoding gradient.

Advantageously, a pulse with inverted polarity during the capture, as what is known as a bipolar or "balanced" motion encoding gradient, provides that artifacts, for instance those caused by the susceptibility of metals or by susceptibility jumps between different tissue types or tissue and air, are canceled out because of the inverted sign, leaving just the motion-dependent effects.

In an embodiment of the method, the method additionally includes capturing a temperature magnetic resonance image of the target area by image capture by the magnetic resonance tomography unit using a temperature-sensitive sequence. This may be ascertained by analyzing the temperature-dependent change in the Larmor frequency or a temperature-dependent change in the T1 relaxation time. In a further act, a temperature map of the target area is ascertained from the temperature magnetic resonance image.

A radiation dose ascertained by the movement may be verified advantageously by its heating effect. Also, the effect of the radiation on the tumor is temperature dependent, and therefore a better estimate may be made of the action of the radiation dose, and the radiation dose may be optimized or reduced for the same therapeutic success.

In an embodiment of the method, a position of a target tissue, for instance a tumor, or even of an adjacent organ to be protected, is ascertained from one of the captured magnetic resonance images, and further irradiation carried out depending on the ascertained position. Through natural movement of the body, for instance breathing, heartbeat, or peristalsis, but also through deliberate movements, the location of a tumor may change during a treatment and in particular between different treatment appointments as a result of treatment-related shrinking, even with careful external marking and positioning, with the result that the irradiation does not hit, or does not entirely hit, the target, for instance the tumor, and instead damages adjacent vital organs.

Since the magnetic resonance tomography unit using the image capture for ascertaining the dose also simultaneously captures a spin distribution for a "normal" image, for instance when an analysis is carried out without forming the difference, it is advantageously possible to use this quasi real-time imaging and to adapt the irradiation advantageously whether by realigning the irradiation device, the patient or just by pausing, for instance during breathing or heartbeat, until the tumor and/or adjacent organs again have the predefined position in the irradiation plan.

In an embodiment of the method, the method additionally includes achieving predefined heating in the target area by a radiofrequency signal from the magnetic resonance tomography unit. The radiofrequency pulses needed to excite the nuclear spins lead to heating of the body tissue as a result of the absorbed radiofrequency energy. The heating may be influenced by suitable design of the radiofrequency pulses, for example, through emission via a plurality of antennas for spatial variation, or additional radiofrequency pulses, in order to achieve a predefined temperature rise in a predefined target area.

The action of the irradiation on the tissue may advantageously be optimized by an increase in temperature. Furthermore, this effect may be adjusted and monitored more precisely using the above-presented thermometry by magnetic resonance imaging.

The following description of the embodiments, which are explained in greater detail in conjunction with the drawings, clarify and elucidate the above-described properties, features, and advantages of this disclosure, and the manner in which they are achieved.

DETAILED DESCRIPTION

Figure 1:
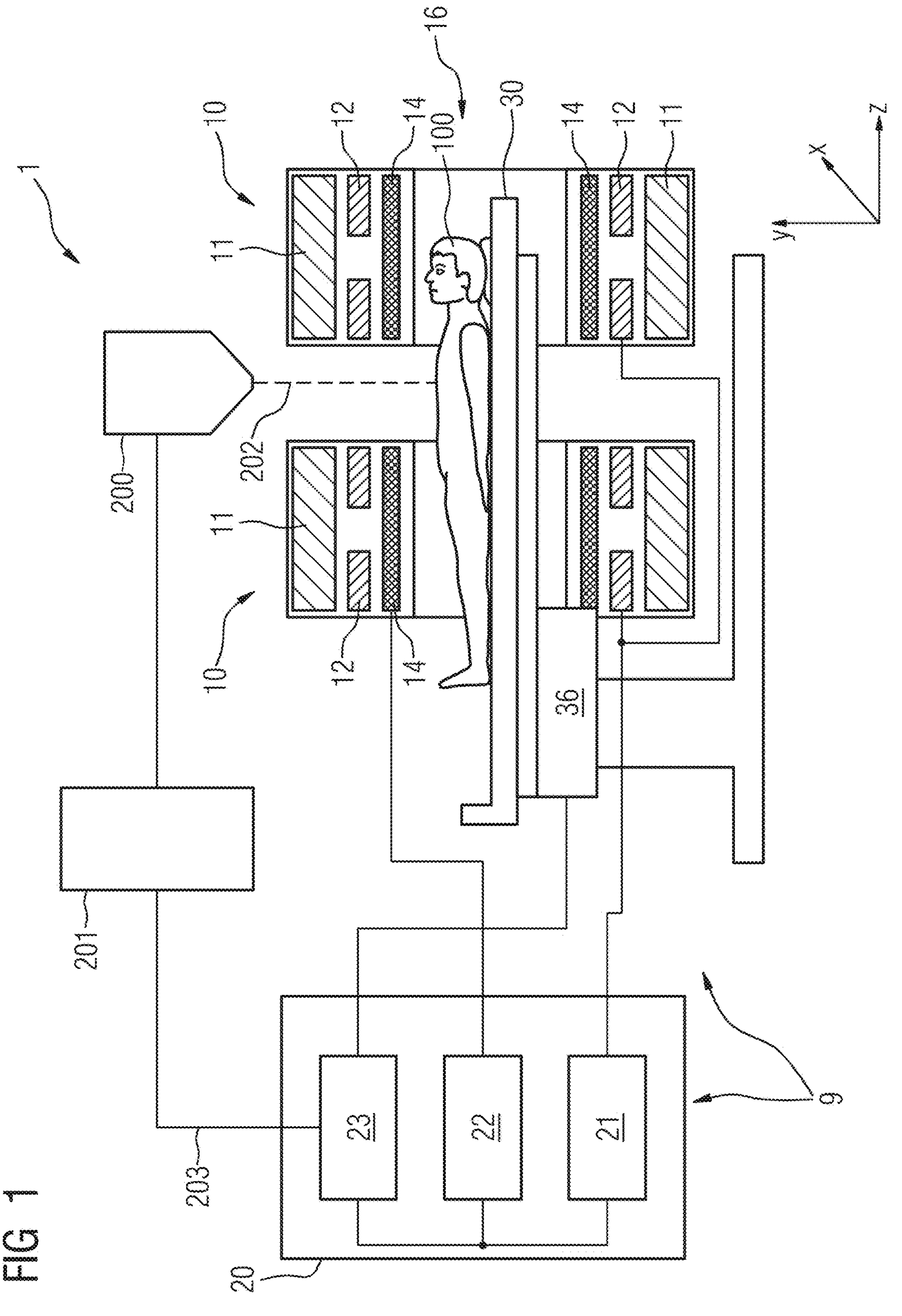
FIG. 1 depicts a schematic representation of an example of a device.

FIG. 1 shows a schematic representation of an embodiment of a device for real-time monitoring of an applied dose.

The device in FIG. 1 has a magnetic resonance tomography unit 9 and an irradiation device 200, the control units 20, 201 of which are connected to each other via a signal connection 203 in order to carry out the real-time monitoring of the method.

The magnet unit 10 of the magnetic resonance tomography unit 9 has a field magnet 11, which produces a static magnetic field B0 for aligning nuclear spins of samples or patients 100 in an acquisition region. FIG. 1 shows the magnet unit 10 by way of example as a horizontal split magnet, e.g., the magnet unit 10 is split or divided into two parts, so that the irradiation device 200 has unobstructed access to the patient 100 for the irradiation. Other embodiments of the magnet unit 10 are also conceivable that allow access for the irradiation at the same time as image capture in the target area, for example, also vertical split-magnet systems or single-piece magnet units 10 containing suitable apertures. In principle, radiation sources as the irradiation device 200 are also conceivable inside the magnet unit 1, provided their radiation intensity may be modulated and they are compatible with the image capture.

The acquisition region of the magnetic resonance tomography unit is arranged in a patient tunnel 16, which extends through the magnet unit 10 in a longitudinal direction 2. As already mentioned above, the patient tunnel 16 is at least discontinuous, (e.g., at least in parts), so that the patient is accessible for irradiation by the irradiation device 200. The acquisition region is in a region that also includes the target area of the irradiation in the patient 100.

The patient 100 may be moved into the acquisition region by the patient couch 30 and the travel unit 36 of the patient couch 30. The field magnet 11 may be a superconducting magnet, which may provide magnetic fields having a magnetic flux density of up to 3 T or even higher in the latest equipment. For lower field strengths, however, permanent magnets or electromagnets having normal-conducting coils may also be used.

The magnet unit 10 also has gradient coils 12, which are configured to superimpose variable magnetic fields in three spatial dimensions on the magnetic field B0 for the purpose of spatial discrimination of the captured imaging regions in the volume of interest. The gradient coils 12 may be coils made of normal-conducting wires, which may generate fields with mutually orthogonal gradients in the volume of interest.

The magnet unit 10 also includes a body coil 14, which is configured to radiate into the acquisition region a radiofrequency signal supplied via a signal line, and to receive resonance signals emitted by the patient 100 and to output the resonance signals via a signal line. For the emission of the radiofrequency signal and/or the receiving, however, the body coil 14 may be replaced by local coils, which are arranged in the patient tunnel 16 close to the patient 100. It is also conceivable, however, for the local coil to be configured for sending and receiving, and therefore a body coil 14 may be omitted.

A control unit 20 supplies the magnet unit 10 with the various signals for the gradient coils 12 and the body coil 14, and analyzes the received signals. A magnetic-resonance-imaging unit controller 23 coordinates the sub-units in this process.

Thus the control unit 20 has a gradient controller 21, which is configured to supply the gradient coils 12 via supply lines with variable currents that provide, coordinated in time, the desired gradient fields in the volume of interest.

In addition, the control unit 20 has a radiofrequency unit 22, which is configured to produce a radiofrequency pulse having a temporal variation, amplitude and spectral power distribution for the purpose of exciting magnetic resonance of the nuclear spins in the patient 100. Pulse powers may reach in the region of kilowatts here. The individual units are interconnected via a signal bus.

The radiofrequency signal produced by the radiofrequency unit 22 is fed via a signal connection to the body coil 14, and radiated into the body of the patient 100 in order to excite nuclear spins there. It is also conceivable, however, to emit the radiofrequency signal via one or more local coils.

The local coil then may receive a magnetic resonance signal from the body of the patient 100, because, as a result of the small distance, the signal-to-noise ratio (SNR) of the local coil is better than when using the body coil 14 for reception. The MR signal received by the local coil is conditioned in the local coil and passed to the radiofrequency unit 22 of the magnetic resonance imaging unit 1 for analysis and image capture.

The irradiation device 200 is arranged relative to the magnetic resonance tomography unit 9 in such a position that a beam may reach a target area in an acquisition region of the magnetic resonance tomography unit 9. In the case of a split magnet, the irradiation device 200 may be moved along a path around the target area in order to reduce damage to tissue around the target, for instance, a tumor.

The irradiation device 200 is capable of modulating the intensity of the emitted radiation in a predefined manner at an acoustic frequency, for example, in a frequency range of 1 Hz to 100 kHz or in a range of 10 Hz to 10 kHz. An X-ray source or an accelerator is conceivable in which the intensity may be varied by a current of the ion or electron source. Radiation sources containing an isotope would also be conceivable provided modulation or breaks at the stated frequencies may be achieved in a predefined manner by a controllable shutter.

Figure 2:
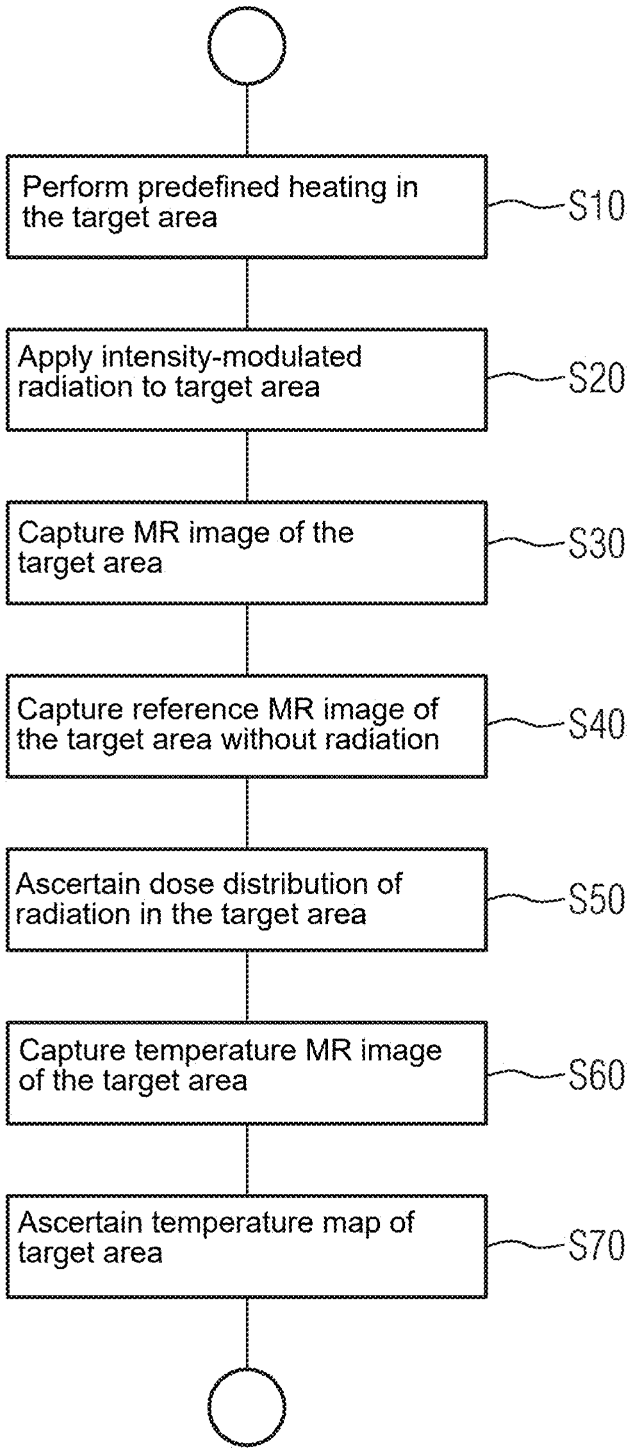
FIG. 2 depicts a schematic flow diagram of an example of a method.

FIG. 2 shows schematically a flow diagram of an embodiment of the method.

In act S20, intensity-modulated radiation is applied to the target area by the irradiation device 200. The modulation is performed at an acoustic frequency, e.g., in a range of 1 Hz to 100 kHz or in a range of 10 Hz to 10 kHz. The modulation has a predefined time or phase relationship with image capture by the magnetic resonance tomography unit 9, i.e., the modulation is synchronized with the image capture. The synchronization is performed by a signal connection 203 between a controller 23 of the magnetic resonance tomography unit 9 and a control unit 201 of the irradiation device 200.

In act S30, the magnetic resonance tomography unit 9 captures a magnetic resonance image of the target area during application of the radiation. "During" may be understood to mean here that the magnetic resonance image includes at least the time period of applying the radiation, so that the magnetic resonance image may capture an entire applied radiation dose. In certain examples, time segments of applying the radiation may be synchronized, or may take place simultaneously, with time segments of the image capture that are sensitive to a deflection of the tissue or of the nuclear spins contained therein.

Figure 3:
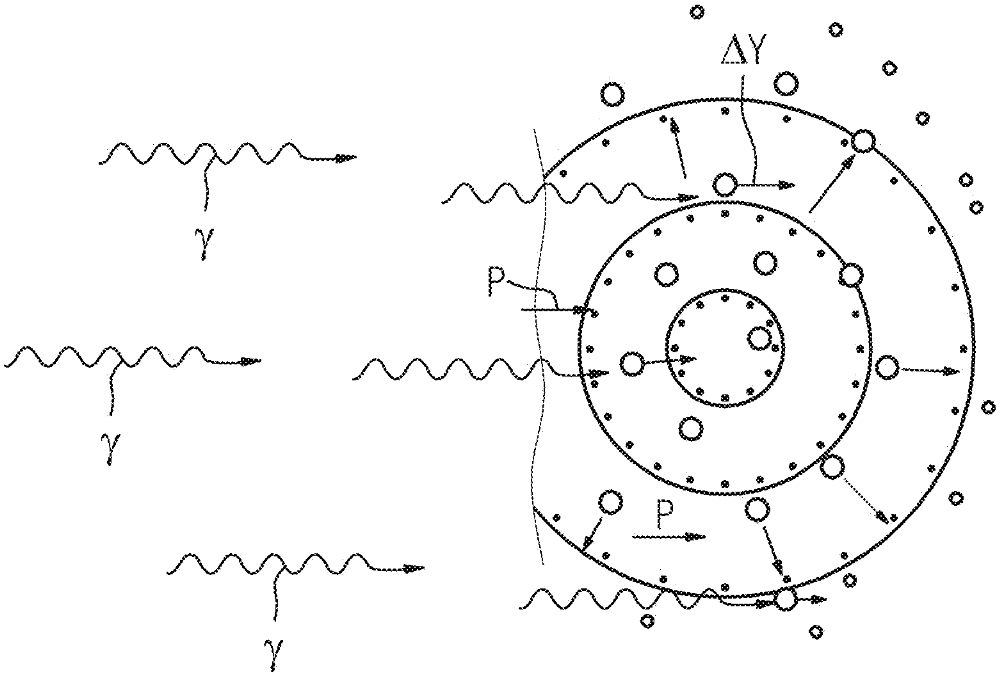
FIG. 3 depicts a schematic representation of an example of the action of radiation on tissue in a patient.

FIG. 3 shows schematically how the incident radiation in the tissue leads to a deflection. The incident radiation, whether X-ray quanta or gamma quanta or even high-energy particles, inputs both energy and a momentum P into the tissue. If the radiation in the tissue is scattered or absorbed by the atoms, most of the energy is converted into heat, which leads to thermal expansion that makes tissue expand about a center of maximum energy input, as indicated in FIG. 3 by the concentric circles. The expansion causes a radial movement in all directions from this center. These geometric relationships have to be taken into account when ascertaining the radiation dose from the captured deflection, in particular if the thermal effect predominates.

All or some of the momentum P is also transferred to the atoms, and a force is exerted on the atoms, which in turn may cause a movement along the beam direction, as indicated by the arrows labeled with Δy. Since the atoms are elastically bound in the tissue, the force may likewise lead to a deflection. Which effect predominates depends, inter alia, on the nature of the radiation and its energy. For example, ion radiation leads to a higher momentum transfer because of the high rest mass of the particles.

For the non-oscillatory deflection, the deflection may be modeled as follows:

$$a(\vec{r}, t) = \begin{cases} a_{max} \cdot \left(1 - e^{-\frac{t-t_1}{\tau_{rise}}}\right), & t_1 \le t \le t_2 \\ a_{pk} \cdot e^{-\frac{t-t_{OFF}}{\tau_{decay}}}, & t > t_2 \end{cases}$$

wherein the time constants $\tau_{rise}$ and $\tau_{decay}$ relate to the elastic properties of the tissue.

In muscle tissue, the rise time constant $\tau_{rise}$ is 3.2 ms, for example, and the decay time constant $\tau_{decay}$ 5.5 ms. In liver tissue, the rise time is 6.2 ms and the decay time is 7.9 ms. The parameter $a_{max}$ is the quasi-static maximum of the deflection for prolonged irradiation.

The parameter $$a_{pk} = a_{max} \cdot \left(1 - e^{-\frac{t_2-t_1}{\tau_{rise}}}\right)$$

ves the maximum deflection of the tissue reached at the end of a radiation pulse.

Figure 4:
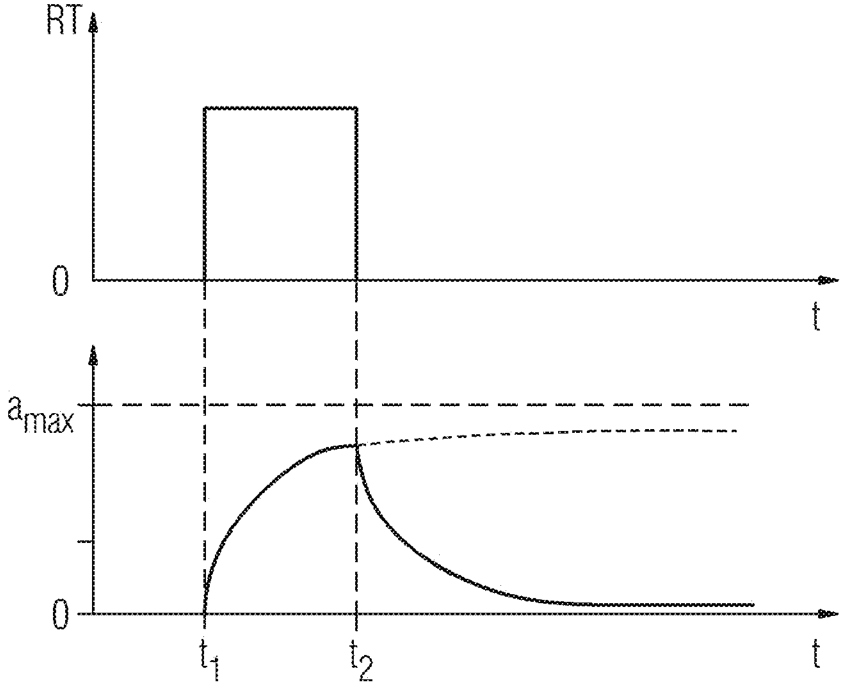
FIG. 4 depicts an example of a time relationship between radiation and deflection.

FIG. 4 shows schematically the time relationship between the incident radiation and the tissue deflection that it produces. The modulated radiation is shown for the sake of simplicity as a rectangular pulse, which is defined by switch-on of the radiation source at a predefined time t1 and switch-off at a predefined time t2.

The thermal effect in terms of its variation over time is determined primarily by the thermal capacity and thermal conductivity properties of the tissue. The temperature, and hence the thermal expansion and deflection, of a volume element increases with rising temperature resulting from the energy supplied by the radiation. At the same time, heat dissipation increases with temperature difference. The deflection initially increases steeply and proceeds asymptotically to a state of equilibrium unless the beam is stopped first. After the stoppage, the temperature drops through thermal diffusion to the body temperature again in an asymptotic curve.

On the other hand, a force caused by a pulse of the radiation takes effect instantaneously with the start of the radiation and is approximately constant over time. The tissue follows the model of a damped pendulum. The damping is caused by the viscosity of the tissue and the restoring force is caused by the elasticity of the tissue for transverse movement. FIG. 4 shows the case in which the viscosity of the tissue leads to an asymptotic oscillation. With switch-on of the radiation, the deflection heads asymptotically towards a maximum equilibrium-value $a_{max}$, and after switch-off of the beam decays asymptotically towards 0 again.

In this regard, the example curve of the deflection in FIG. 4 is qualitatively comparable for both cases and depends largely on the properties of the beam, the tissue, and the beam duration.

Figure 5:
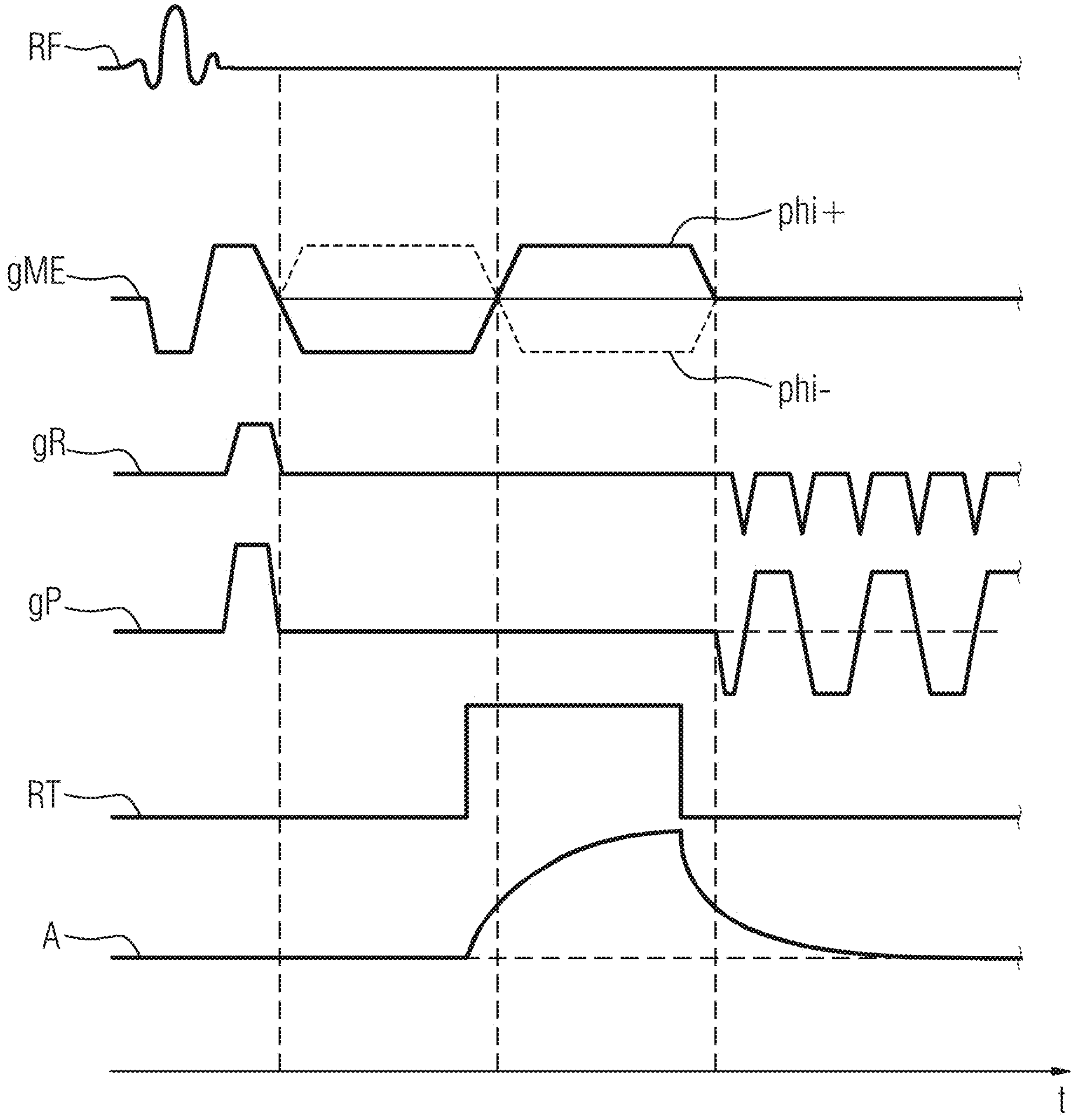
FIG. 5 depicts a diagram of an example variation over time of a GRE-EPI sequence.
Figure 6:
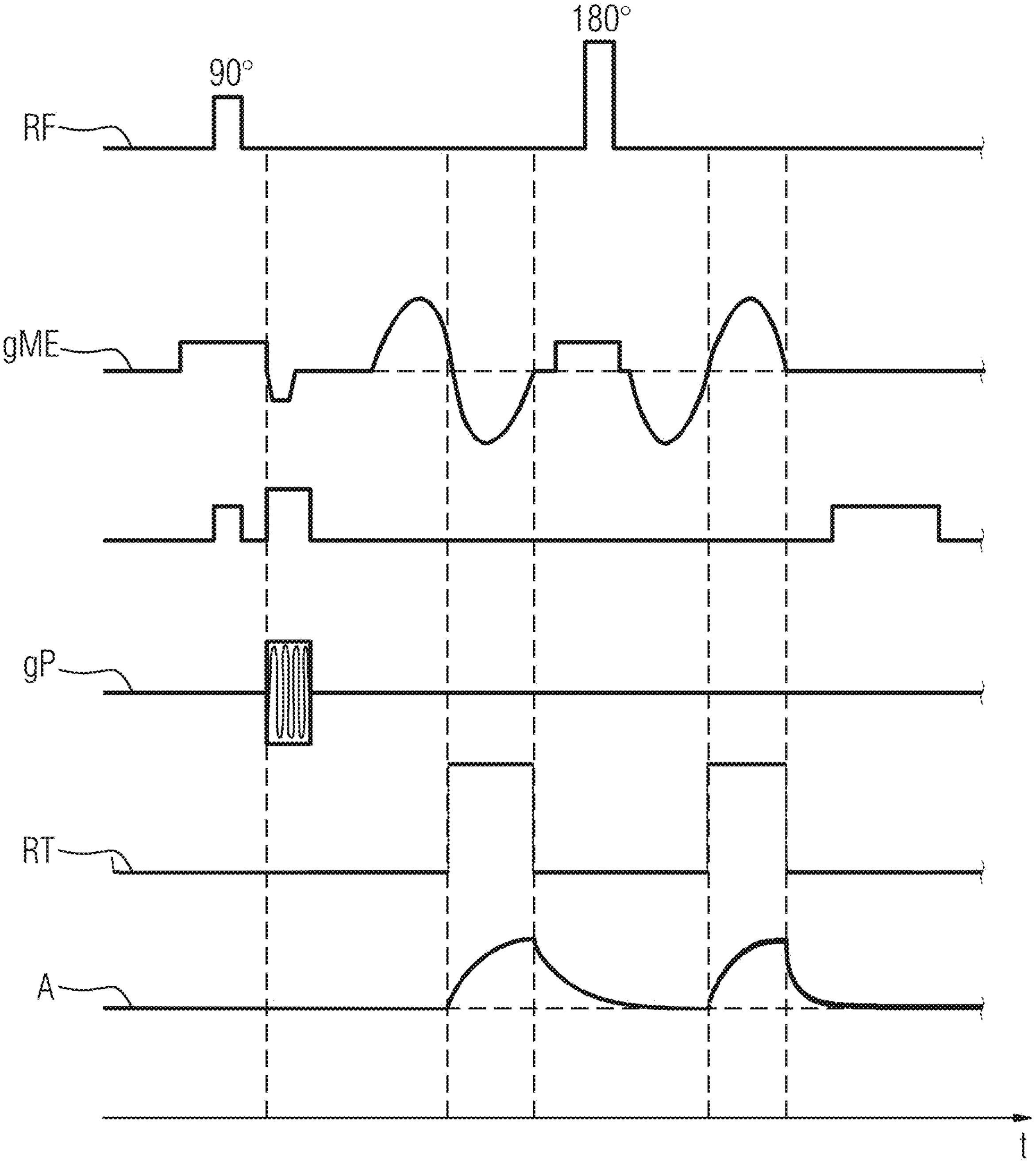
FIG. 6 depicts a diagram of an example variation over time of a modified SE sequence.
Figure 7:
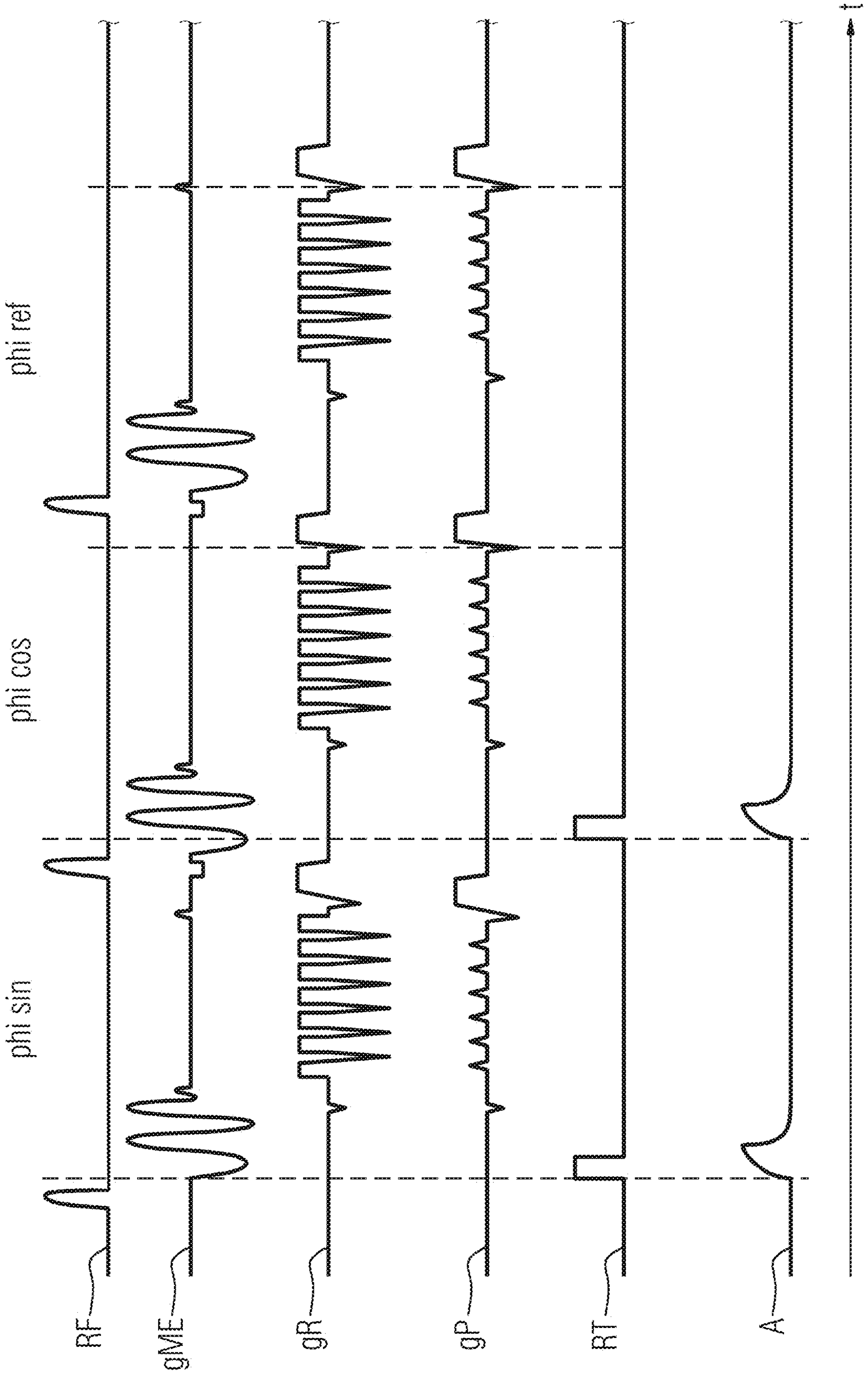
FIG. 7 depicts a diagram of an example variation over time of a modified EPI sequence.

The subsequent figures, FIG. 5 to FIG. 7, give different examples of suitable sequences and timings.

In act S50, a dose distribution of the radiation in the target area is ascertained on the basis of the captured amplitude of the deflection. In one example, the deflection is proportional to the radiation intensity or to the power. Consequently, the radiation dose is proportional to an integral of the deflection over time. As explained below with reference to the sequences, the integral may be implemented already by the sequence. Alternatively, it is conceivable to perform the integral numerically. A proportional factor may be performed, for example, by a calibration sequence on a phantom using a defined radiation dose.

In act S40, a reference magnetic resonance image of the target area may be captured using the magnetic resonance tomography unit 9 without the irradiation device 200 applying radiation. A reference image is thereby acquired that reproduces influences caused by the patient 100 and inhomogeneities in the image capture by the magnetic resonance tomography unit 9. These inhomogeneities may be eliminated advantageously, for example, by forming the difference in act S50 (determining the dose distribution) between the magnetic resonance image with radiation applied and reference magnetic resonance image without radiation applied.

In order to capture the deflection in the magnetic resonance image, as explained in greater detail below with reference to the example sequences, motion encoding gradients (MEG) are used that produce a phase deviation in the magnetic resonance signals from the deflection of the tissue. However, the motion encoding gradients may produce similar phase changes as a result of susceptibility jumps in the tissue. Since the susceptibility effects change their sign with the polarity of the gradients, unlike those caused by the deflection, in an embodiment, the act S30 of capturing the magnetic resonance image and the act S40 of capturing the reference magnetic resonance image are repeated, respectively, with an inverted polarity of a phase encoding gradient. Then, in act S50, both the magnetic resonance images and the reference magnetic resonance images with both polarities of the motion encoding gradients are used to correct the susceptibility effects in determining the dose distribution.

In certain examples, in act S10, a radiofrequency signal of the magnetic resonance tomography unit may be used to perform predefined heating in the target area. For example, a body coil having a multiplicity of transmit channels or having a local transmit array may achieve a predefined field distribution, which, as a result of absorption of the radiofrequency waves, achieves predefined heating in the target area. It is also conceivable, however, that the predefined heating takes place during or after irradiation by the radiation pulse.

In addition, in certain examples, in act S60, a temperature magnetic resonance image of the target area may be captured by image capture using a temperature-sensitive sequence, and in a further act S70, a temperature map of the target area is ascertained from the temperature magnetic resonance image.

Some possible sequences that have sensitivity for capturing a deflection are presented below.

FIG. 5 shows schematically by way of example the variation over time of signals in a GRE-EPI sequence in time correlation with the irradiation, and its detectable effect on the tissue.

The time axis runs from left to right. Vertical lines are inserted to emphasize in particular simultaneous events. The sequence is not shown in full over time, as indicated by the break lines on the right, but just a representative start of the sequence.

RF denotes the radiofrequency signal applied to the patient 100 for exciting the nuclear spins. In the GRE-EPI sequence, first a radiofrequency pulse takes place for exciting a predefined slice, simultaneous with a slice selection gradient.

Underneath in FIGS. 5 to 7 are plotted three gradient signals, gME, gR, and gP. The notations x, y, and z are not chosen here because the axes are fundamentally interchangeable according to the direction in which a deflection is meant to be captured.

gME denotes here the gradient used for the motion encoding. For the GRE sequence, the motion encoding is performed using the same gradient that is used for slice selection during the excitation of the nuclear spins. gR denotes the gradient used for the readout, and gP denotes the gradient used for the phase encoding. The gradients of the vector fields produced by the gradient coils may span a Cartesian coordinate system, with a 2D slice being sampled in the plane spanned by gR and gP. The strength of the gradients is plotted in arbitrary units, with positive and negative polarities shown with respect to the rest line.

RT shows the variation over time of the radiation intensity of the irradiation device 200 in arbitrary units. For the sake of simplicity, a pulse from switching the beam on and off is assumed here.

The amplitude of the deflection in the tissue is given by A. As already explained with reference to FIG. 4, the deflection begins with the radiation and returns to the rest position once the radiation ends.

In the GRE-EPI sequence, the encoding is performed by gME with one polarity of the gradient in a segment without any radiation or deflection induced thereby, and with a reverse polarity of the gradient in a segment with radiation or deflection. Effects that are not related to deflection may be reduced by forming the difference between the signals, thereby increasing the sensitivity for the deflection. In a repetition of the sequence shown, sampling is performed with inverted polarities, as indicated by the curves denoted by phi+ and phi−. The deflection may hence be captured using different gradient field directions. Such balanced gradient pulses, as they are known, make it possible to distinguish the effects of the deflection from signals induced by susceptibility jumps, because the direction or polarity of the signals induced by susceptibility jumps also changes direction or polarity with the inverted polarity. Susceptibility effects may thereby also be reduced by forming the difference.

The following relationship is obtained for a phase change of nuclear spins:

$$\Delta\varphi(\vec{r}, t) = \gamma \int_0^t \overrightarrow{MEG}(\vec{r}, \tau) \cdot \vec{u}(\vec{r}, \tau) d\tau$$

where φ is the phase, $\vec{r}$ is the location of a nuclear spin, $\overrightarrow{MEG}(\vec{r},\tau)$ is the gradient gME as a function of location and time, $\vec{u}(\vec{r},\tau)$ is a vector for the deflection of a nuclear spin as a function of rest location and time, and γ is a gyromagnetic factor.

For bipolar and "balanced" MEG and without deflection in the tissue during the MEG, the term equals zero.

The sequence may be repeated 4 times: a first time with positive MEG pulses superimposed on the slice selection pulses (in FIG. 5 denoted by phi+ for gME); a second time with positive MEG but without radiation pulses RT; a third time with negative MEG pulses (in FIG. 5 denoted by phi− for gME); and a fourth time again without radiation pulses RT. The four cumulative phase shift maps that are captured respectively with these four magnetic resonance sequences are:

$$\begin{cases} \phi^{+}(x, y) & \text{with positive } MEG \\ \phi^{0+}(x, y) & \text{and without } RT \text{ pulses} \\ \phi^{-}(x, y) & \text{with negative } MEG \\ \phi^{0-}(x, y) & \text{and without } RT \text{ pulses} \end{cases}$$

The maps with the phase background captured without a radiation pulse provide the calibration data for correcting eddy current effects, because the EPI sequences are very sensitive to leakage fields from conductors in the surrounding area, which are caused by the gradient fields.

Hence the deflection map for the tissue is given by:

$$a(x, y) = \frac{\phi^{+}(x, y) - \phi^{0+}(x, y) - \phi^{-}(x, y) + \phi^{0-}(x, y)}{\gamma \cdot G_{MEG} \cdot 2\delta}$$

where $G_{MEG}$ is the amplitude and 2δ is the duration of the MEG pulses

This yields a temperature map given by $$\Delta T(x, y) = \frac{\phi^{+}(x, y) - \phi^{0+}(x, y) + \phi^{-}(x, y) - \phi^{0-}(x, y)}{\gamma \cdot TE \cdot B_0 \cdot 2\alpha}$$

where α=−0.0094 ppm/° C. is the temperature coefficient for the shift in the photon resonant frequency (PRFS), TE is the echo time, and B0 is the strength of the static magnetic field B0 in Tesla.

FIG. 6 shows an example of a standard magnetic resonance sequence SE modified for sensitivity to tissue deflection.

The RF radiofrequency pulses have a 90° pulse for flipping the magnetization into the transverse plane, followed by a 180° refocusing pulse, both made at the Larmor frequency or resonant frequency (e.g., 64 MHz for a 1.5 T magnetic resonance tomography unit).

In addition, the gradients for increasing deflection sensitivity are added to the standard sequence in the slice selection direction in order to encode the radiation-dependent deflection. These are shown as sinusoidal pulses on gME.

A second radiation pulse is triggered synchronously with the second MSG period in order to cause a synchronous deflection of the tissue and to minimize the radiation pulse duration. The intensity and the duration of the radiation pulse RT is chosen such that the sequence produces a sufficient deflection of the tissue for capture while still being low enough to minimize tissue damage. The MR signals containing the accumulated phase shift are then captured during the readout window.

FIG. 7 shows a further modified EPI sequence, which takes into account the influence of further tissue deflections that are not induced by the radiation, for instance caused by breathing or a heartbeat. The rapid succession of three EPI sequences captures the phase accumulation in the reconstructed magnetic resonance images with sine and cosine modulated MEG pulses and in a third magnetic resonance image with MEG pulses but without radiation pulses. This last sequence measures the accumulated phase background caused by other forms of slower movement. The sine and cosine modulated gradient pulses advantageously reduce both eddy current effects and the acoustic noise emitted by the gradient pulses.

Further variations of sequences that achieve a sensitivity to tissue deflections are also conceivable within the context of the disclosure. In particular, other sequences already used in the context of elastography are conceivable. Sequences are likewise conceivable that are employed as part of image capture using contrast agents.

In addition, sequences are conceivable that are used for diffusion measurement, because in particular these are not limited to a predefined linear direction of movement but also capture a spherically symmetrical movement caused by thermal expansion.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for monitoring in real time, by a magnetic resonance tomography unit, a radiation dose applied by an irradiation device in a target area, the method comprising:

applying intensity-modulated radiation to the target area by the irradiation device in a form that is modulated in intensity in an acoustic frequency range, wherein the intensity-modulated radiation causes a deflection of tissue in the target area;

capturing, by the magnetic resonance tomography unit, a magnetic resonance image of the target area during application of the intensity-modulated radiation, wherein the magnetic resonance tomography unit employs a sequence that captures an amplitude of the deflection of the tissue in the target area; and ascertaining a dose distribution of the intensity-modulated radiation in the target area based on the captured amplitude of the deflection of the tissue.

2. The method of claim 1, further comprising:

capturing a reference magnetic resonance image of the target area without radiation applied, wherein the dose distribution is ascertained based on the magnetic resonance image and the reference magnetic resonance image.

3. The method of claim 2, wherein a sequence containing motion encoding gradients is used in the capturing of the magnetic resonance image and in the capturing the reference magnetic resonance image, and wherein the capturing of the magnetic resonance image and/or the capturing the reference magnetic resonance image is performed with an inverted polarity of a phase encoding gradient.

4. The method of claim 1, wherein a sequence containing motion encoding gradients is used in the capturing of the magnetic resonance image, and wherein the capturing of the magnetic resonance image is performed with an inverted polarity of a phase encoding gradient.

5. The method of claim 1, further comprising:

capturing a temperature magnetic resonance image of the target area by image capture using a temperature-sensitive sequence; and ascertaining a temperature map of the target area from the temperature magnetic resonance image.

6. The method of claim 1, further comprising:

ascertaining a position of a target tissue from one of the captured magnetic resonance images; and carrying out further irradiation depending on the ascertained position of the target tissue.

7. The method of claim 1, further comprising:

achieving predefined heating in the target area by a radiofrequency signal from the magnetic resonance tomography unit.

8. A system for monitoring in real time a radiation dose, the system comprising:

an irradiation device; and a magnetic resonance tomography unit, wherein the irradiation device is configured to emit and apply a radiation to a target area, wherein the radiation is in a form that is modulated in intensity in an acoustic frequency range, and wherein the radiation is configured to cause a deflection of tissue in the target area, wherein the magnetic resonance tomography unit is configured to capture a magnetic resonance image of the target area during application of the radiation, wherein the magnetic resonance tomography unit employs a sequence configured to capture an amplitude of the deflection of the tissue in the target area, wherein the applying of the radiation and the capturing of the magnetic resonance image are configured to be synchronized, and wherein the system is configured to ascertain a dose distribution of the radiation in the target area based on the captured amplitude of the deflection of the tissue.

9. The system of claim 8, wherein the magnetic resonance tomography unit is additionally configured to capture a reference magnetic resonance image of the target area without radiation applied, and wherein the dose distribution is ascertained based on the magnetic resonance image and the reference magnetic resonance image.

10. The system of claim 9, wherein the magnetic resonance tomography unit is configured to use a sequence containing motion encoding gradients in the capturing of the magnetic resonance image and/or the capturing of the reference magnetic resonance image, and wherein the capturing of the magnetic resonance image and/or the capturing the reference magnetic resonance image is configured to be performed with an inverted polarity of a phase encoding gradient.

11. The system of claim 8, wherein the magnetic resonance tomography unit is configured to use a sequence containing motion encoding gradients in the capturing of the magnetic resonance image, and wherein the capturing of the magnetic resonance image is configured to be performed with an inverted polarity of a phase encoding gradient.

12. The system of claim 8, wherein the magnetic resonance tomography unit is further configured to:

capture a temperature magnetic resonance image of the target area by image capture using a temperature-sensitive sequence; and ascertain a temperature map of the target area from the temperature magnetic resonance image.

13. The system of claim 8, wherein the system is configured to ascertain a position of a target tissue from one of the captured magnetic resonance images, and wherein the irradiation device is configured to carry out further irradiation depending on the ascertained position.

14. The system of claim 8, wherein the magnetic resonance tomography unit is further configured to achieve predefined heating in the target area by a radiofrequency signal from the magnetic resonance tomography unit.

15. A non-transitory electronically readable data storage medium comprising a computer program product, wherein the computer program product comprises a program configured to be loaded directly into a memory of a programmable controller of a system, wherein the program, when executed in the controller, is configured to cause the system to:

apply intensity-modulated radiation to a target area by an irradiation device of the system in a form that is modulated in intensity in an acoustic frequency range, wherein the intensity-modulated radiation is configured causes a deflection of tissue in the target area;

capture, by a magnetic resonance tomography unit of the system, a magnetic resonance image of the target area during application of the intensity-modulated radiation, wherein the magnetic resonance tomography unit employs a sequence that captures an amplitude of the deflection of the tissue in the target area; and ascertain a dose distribution of the intensity-modulated radiation in the target area based on the captured amplitude of the deflection in the target area.

16. The method of claim 1, wherein the deflection of the tissue is an expansion of the tissue resulting from heating from application of the intensity-modulated radiation.

17. The method of claim 1, wherein the deflection of the tissue is caused by a direct transfer of momentum from particle beams of the intensity-modulated radiation.

* * * * *